United States Patent [19]

Kozin et al.

[11] Patent Number: 4,766,904
[45] Date of Patent: Aug. 30, 1988

[54] APPLANATION TONOMETER

[75] Inventors: Mikhail P. Kozin; Nikolai V. Kudashov; Jury I. Sakharov, all of Kuibyshev; Svyatoslav N. Fedorov, Moscow, all of U.S.S.R.; 1

[73] Assignees: Kuibyshevsky Politeknichesky Institute, Kuibyshev; Moskovsky Nauchno-Issledovatelsky Institute Mikrohirurgii Glaza, Moscow, both of U.S.S.R.

[21] Appl. No.: 15,618

[22] Filed: Feb. 17, 1987

[51] Int. Cl.$^4$ .............................................. A61B 3/16
[52] U.S. Cl. ................................................... 128/652
[58] Field of Search ........................ 128/645, 651, 652

[56] References Cited

U.S. PATENT DOCUMENTS

| 3,308,653 | 3/1967 | Roth ................................... | 128/645 |
| 3,677,074 | 7/1972 | Morr ................................... | 128/645 |
| 3,703,095 | 11/1972 | Holcomb et al. .................... | 128/645 |
| 4,305,399 | 12/1981 | Beal .................................... | 128/645 |

OTHER PUBLICATIONS

Intraocular Pressure (Physiology and Pathology), A. Nestorov et al., Mir Publishers, Moscow (1978).
The Non-Gravimetric Tonometer (Bausch & Lomb)-1981.

Primary Examiner—Edward M. Coven
Attorney, Agent, or Firm—Lilling & Greenspan

[57] ABSTRACT

An applanation tonometer comprises a housing, a rod accommodated in the housing and carrying a contact disk adapted to interact with the corneal surface in order to exert force thereon, a unit for measuring the force applied to the cornea, a means for registering the instant of time when the diameter of an applanation circle on the corneal surface formed due to the effect of a force applied thereto reaches a preset value, and a recording unit. The registering means is made as a sleeve arranged coaxially with the rod carrying the contact disk and traversably along the rod axis, and a contact set electrically connected to the recording unit and mechanically associated with the traversable sleeve. An additional sleeve is traversable, set coaxially with the traversable sleeve of the registering means, and the end of said additional sleeve is concave-shaped.

2 Claims, 1 Drawing Sheet

U.S. Patent  Aug. 30, 1988  4,766,904
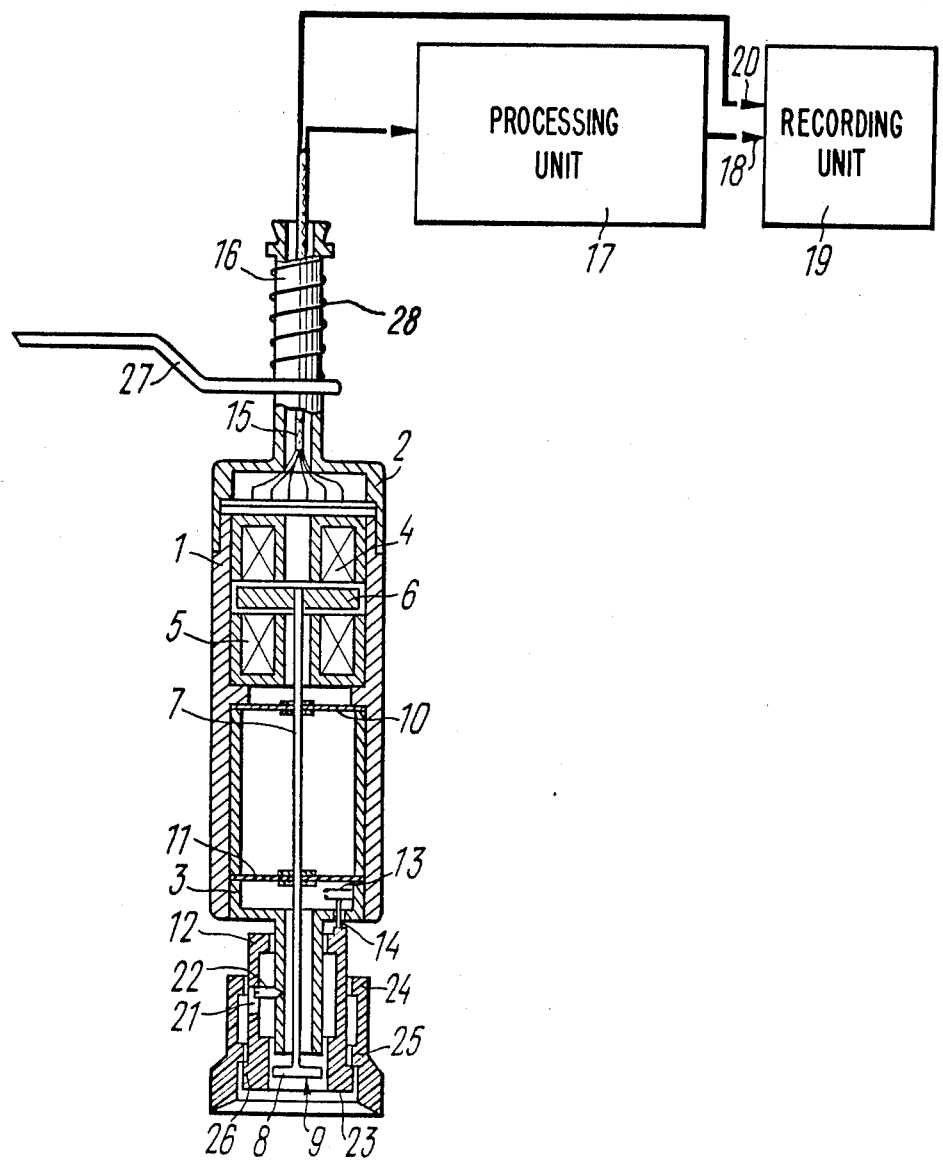

APPLANATION TONOMETER

FIELD OF THE INVENTION

This invention relates generally to medical apparatus and more specifically it concerns applanation tonometers applied in ophthalmology for measuring intraocular pressure and the values of hydrodynamic coefficients (that is, the aqueous outflow facility coefficient C and the aqueous minute volume F).

BACKGROUND OF THE INVENTION

All the heretofore-known applanation tonometers may be subdivided into tonometers featuring a constant pressure applied to the corneal surface to flatten it, and those featuring a variable force applied to the corneal surface with the same purpose. In the former-type tonometers a measure of the intraocular pressure is the diameter of an applanation circle which is meant as an averaged diameter of an impression or indentation corresponding to a flattened area of the corneal surface resulting from the effect of a known constant force applied to the cornea, e.g., gravitational force. Most commonly used tonometers of that type are such as, e.g., Maklakov's Filatov-Kalfa's (cf. A. Nesterov et al. "Intraocular pressure (physiology and pathology)", Mir Publishers, Moscow, 1978, pp. 21–22).

However, the aforementioned tonometers suffer from too sophisticated calibration and low measuring accuracy due to an adverse effect of the corneal rigidity forces and of a ring of the lacrimal fluid arising round the applanation circle.

The latter-type tonometers may be exemplified by those of Goldmann's, Mackey's, Marg's, Draeger's (cf. A. Nesterov et al., op. cit., pp. 21–23).

In these tonometers a measure of the intraocular pressure is a force exerted on the cornea to form an applanation circle thereon having a diameter equal to 3.06 mm, or appearance of a dicrotic wave on the curve characteristic of the force applied versus time, i.e., an abrupt change in the recorded curve representing the force applied. Studies performed demonstrate that the data obtained from measurement of intraocular pressure with the aid of Mackey-Marg tonometer agree with those obtained with the aid of Goldmann's or Draeger's tonometer, the latter being a portable modification of the former tonometer. However, the Mackey-Marg tonometer suffers from the fact that its measuring circuit is too complicated in manufacture due to a stringent requirement imposed on it as to high sensitivity thereof.

When using a Goldmann's tonometer, the instant when the diameter of the applanation circle becomes equal to 3.06 mm is registered visually and the force of pressure exerted on the corneal surface is measured at that instant.

In this case the surface tension forces and the corneal rigidity forces are mutually balanced, therefore the force applied to the applanation area from the side of the tonometer is equal to a true intraocular pressure. The measurement accuracy is increased due to use of a corneal microscope and fluoroscein with which lacrimal fluid is stained.

However, necessity for use of fluorescein complicates operation with Goldmann's tonometer.

Besides, the aforelisted tonometers of the second type are adapted largely for measuring intraocular pressure alone and their application for measuring the hydrodynamical coefficients C and F is rather difficult.

One more applanation tonometer is known to comprise a housing, a rod accommodated in the housing and carrying a contact disk at one of its ends, one of the surfaces of the disk, i.e., a working surface, being adapted to interact with the cornea and to exert a force thereon, a unit for measuring the force applied, associated with the rod, a means for registering the instant when the diameter of an applanation circle on the corneal surface, formed due to the effect of a force exerted by the contact disk on the cornea, reaches a preset value, and a recording unit connected to the outputs of the measuring unit and of the registering means (cf. a prospectus of Bausch Lomb Co, Mark of leadership, "The non-gravimetric tonometer", 1981).

Intraocular pressure is measured with the aid of this tonometer according to the same technique as is the case with Goldmann's tonometer, i.e., there is measured the force of pressure exerted by the contact disk on the cornea surface at the instant when the diameter of the applanation circle on the corneal surface becomes equal to approximately 3.06 mm.

The means for registering the instant when the diameter of an applanation circle reaches a preset value incorporates a system of holes arranged along the periphery of the contact disk, a flexible envelope interposed between the disk working surface and the cornea, a passage for gas to feed from a gas-containing cylinder, said passage being situated inside the rod. The gas pressure in the system is measured with a pressure gauge that generates an electric signal which is applied to the recording unit made as a recorder.

However, the aforesaid known tonometer requires, for the purpose of an adequately high measuring accuracy, highly accurate manufacture of the components of the registering means which is pneumatic as for its operating principle and features a sophisticated construction. This results in more complicated production of the components of the registering means. In addition, the necessity for use of an inert gas (of the type of freon) free from solids also adds to the difficulties involved in operation of the instrument.

SUMMARY OF THE INVENTION

It is an object of the invention to simplify the construction of an applanation tonometer.

It is another object of the invention to provide high-accuracy intraocular pressure measurement.

It is one more object of the invention to do away with use of a gas in intraocular pressure measurement.

It is still one more object of the invention to attain better centring of the sensor with respect to the patient's eye.

The essence of the invention resides in an applanation tonometer, comprising a housing; a rod accommodated in the housing and carrying a contact disk at one of its ends, one of the surfaces of the contact disk, i.e., a working surface, interacting with the cornea to exert a force thereon; a unit for measuring said force connected to the rod; a means for registering the instant when the diameter of an applanation circle on the corneal surface, formed due to the effect of a force applied by the contact disk to the cornea, reaches a preset value; and a recording unit connected to the outputs of the measuring means and of the registering means. According to the invention, the means for registering the instant when the diameter of the applanation circle reaches a preset value includes a main sleeve having an inside diameter equal to a preset value of the applanation circle diameter and arranged coaxially with the rod carrying the contact disk and traversably along the rod axis, and a contact set electrically connected to the recording unit, mechanically associated with the main sleeve, and so arranged that its contacts are closed at the instant when the working surface of the contact disk and the end of the main sleeve become coplanar.

It is expedient, with a view to improving the centering of the tonometer on the patient's eye, to provide the instrument with an additional sleeve arranged coaxially with the main sleeve, axially traversable with respect to the latter, and having its end opposite to the housing concave-shaped into the fragment of a sphere.

The applanation tonometer, according to the present invention, provides for high-accuracy measurement of intraocular pressure corresponding to the Goldmann's technique, requires no use of an inert gas, features a simple construction, high reliability and convenience in use.

BRIEF DESCRIPTION OF THE DRAWING

In what follows the invention is illustrated by a detailed description of some specific exemplary embodiments thereof and the accompanying drawing, showing a fragmentary sectional view of an electromechanical diagram of the applanation tonometer, according to the invention.

DETAILED DESCRIPTION OF THE INVENTION

The applanation tonometer, as illustrated in the appended drawing, comprises a housing 1 provided with a top cover 2 and a bottom cover 3. Accommodated inside the housing 1 in its top portion is a transducer adapted to convert motion into an electric signal and effected in the herein-considered embodiment on the base of two coaxially arranged armoured magnetic ferrite cores with coils 4, 5 interconnected by virtue of a differentiating circuit, and a magnetic ferrite disk 6 located in a gap between the cores with a possibility of moving along the axis of the coils 4, 5. Held to the center of the ferrite disk with one of its ends is a rod 7 whose other end is brought outside the housing 1 and carries a contact disk 8 rigidly locked in place thereon. An outer surface 9 of the contact disk 8 is flat and is in fact the working surface thereof and interacts with the corneal surface and exerts a force thereon. The diameter of the contact disk 8 is selected to be 3 mm. The rod 7 is held to the housing 1 with the aid of plane-parallel springs 10, 11. In addition, the applanation tonometer of the invention comprises a means for registering the instant when the diameter of an applanation circle on the corneal surface, formed due to the effect of a force applied thereto by the contact disk 8, reaches a preset value (that is, 3.06 mm in this particular case). The means comprises a sleeve 12 arranged coaxially with the rod 7 carrying the disk 8 and traversably along the axis of the rod 7, and a contact set, which is in this particular case a pair of electric contacts 13 mechanically associated with the sleeve 12 through a pusher 14 made fast on the sleeve 12. Electric leads running from the motion-to-electric signal transducer and from the contacts 13 are tied together into a bundle 15 which is brought, through a conduit in a projecting portion 16 of the cover 2, out of the housing 1 and is connected to the inputs of a data processing unit 17, whose output is connected to an input 18 of a recording unit 19. Electric leads running from the contacts 13 are insulation-protected and mounted in the wall of the housing 1, passed over said wall to the bundle 15 (which is conventionally omitted in the Drawing), and then connected to an input 20 of the recording unit 19. The motion-to-electric signal transducer and the data processing unit 17 establish a unit measuring the force exerted by the contact disk 8 on the corneal surface of the patient's eye.

The inside diameter of the sleeve 12 equals a preset value of the applanation circle diameter, that is, 3.06 mm in this particular case. The outside diameter of the sleeve 12 is equal to 7 mm, which corresponds to the applanation circle diameter with the intraocular pressure equal to 10 mm Hg a 10-g load applied to the cornea, i.e., to the lower limit of the intraocular pressure measurement range. A recess 21 is made in the side wall of the sleeve 12, and a stop 22 is built into the cover 3, adapted to interact with the recess 12 so as to retain the sleeve 12 in the bottommost position. The arrangement of the contacts 13 and the length of the pusher 14 are so selected that the contacts 13 become closed at the instant when the working surface 9 of the disk 8 and a bottom end 23 of the sleeve 12 are coplanar.

According to the invention, the tonometer is also provided with an additional sleeve 24 set coaxially with the sleeve 12 outside the latter and axially traversable with the sleeve 12. The end of the sleeve 24 most removed from the housing 1 is shaped as the fragment of a sphere, the radius of curvature of which somewhat exceeds the radius of curvature of the corneal sphere. In the herein-considered embodiment of the tonometer the radius of curvature of the aforesaid sphere is selected to be 12 mm to suit the shape of a human's eyeball. The sleeve 24 has an inner projection 25 which is adapted to interact with an outer projection of the sleeve 12 when the sleeve 24 assumes its bottommost position.

For carrying the tonometer conveiently and placing it on a patient's eye, the housing 1 of the tonometer is provided with a handle 27 having at its end a forked grip with a locator, adapted to interact with the projecting portion 16 of the cover 2. In addition, the handle 27 is associated with the cover 2 of the housing 1 through an elastic member, i.e., a spring 28 in this particular case, which with its top end is held to the cover 2, while its bottom end rests freely upon the grip fork prongs.

The data processing unit 17 comprises series-connected an oscillator, or a frequency discriminator, or else a frequency meter.

In the former case a recorder is made use of as the recording unit 19. In the latter case a signal from the frequency meter output is brought out to a digital printer.

The housing 1 along with the covers 2, 3 and sleeves 12, 24, as well as the contents of the housing 1, will hereinafter be referred to as the tonometer sensor.

Measurement of intraocular pressure and carrying out tonographic examinations with the use of the applanation tonometer, according to the invention, is effected as follows.

Using the handle 27 the sensor is placed on the corneal surface with the concave end of the sleeve 24, and is gradually moved down. As a result, the cornea is smoothly loaded through the contact disk 8. Smooth loading of the cornea, at the expense of the sensor own weight equal to 10 g, is attained thanks to connection of the handle 27 to the top cover 2 of the sensor housing 1 through an elastic member, i.e., the spring 28. As a result of a smooth loading of the cornea, the diameter of the applanation circle on the corneal surface is increased progressively, and the sleeve 12 moves evenly towards the housing 1. Displacement of the rod 7 under the effect of loading results in a signal appearing at the output of the data processing unit 17, said signal owing its origin to an unbalance of the parameters of the coils 4, 5 caused by the displacement of the ferrite disk 6 rigidly coupled to the rod 7. With the applanation circle diameter equal to 3.06 mm, i.e., to the inside diameter of the sleeve 12, the base plane of the main sleeve 12 is brought in coincidence with the plane of the working surface 9 of the contact disk 8. As a result, the pusher 14 closes the contacts 13, whereby a signal is produced for measurement of the amount of displacement of the ferrite disk 6 with respect to the coils 4, 5 and starting the recording of the intraocular pressure value by the recorder (or on a digital printer). The plane-parallel springs 10, 11 are so selected that loading of the cornea within a range of 0 to 10 g corresponds to a linearly varying displacement of the rod 7 and the disk 6 with respect to the coils 4, 5. Thus, a force applied to the contact disk 8 in a vertical direction is measured with the aid of the motion-to-electric signal transducer. Said force (in grams) multiplied by a factor of ten gives the value of intraocular pressure.

With the applanation circle diameter equal to 3.06 mm, i.e., at the instant when the contacts 13 are being closed, intraocular pressure is measured, that approximates its true value at an accuracy consistent with the Goldmann's technique. In response to closing of the contacts 13 the data processing unit 17 produces a signal for storing an electrical quantity brought in correspondence with the amount of displacement of the rod 7 and the disk 6 with respect to the coils 4, 5. The aforesaid quantity is registered either in a digital form or with the aid of a pointer indicator. The circuit parameters of the unit 17 are so selected that the digital representation gives the intraocular pressure value in millimeters of a mercury column, while in the case of analogue representation (in the form of a pointer indicator), the above value is read off an instrument scale graduated in millimeters of a mercury column.

Whenever it is necessary to carry out tonographic examinations, the handle 27 is moved down until it disengages from the elastic member (that is, the spring 28). As a result, the sensor weight (10 g) is fully applied to the eyeball through the contact disk 8 and the bottom end of the sleeve 12, whose top end rests in this case against the surface of the bottom cover 3 of the housing 1. Under such conditions there is recorded intraocular pressure which is measured, as described above, by virtue of displacement of the rod 7 and the ferrite disk 5 with respect to the coils 4, 5. Recording lasts 2 to 4 minutes, whereupon the value of the aqueous outflow facility coefficient C, which is decisive for assessment of the ocular hydrodynamics, is found by way of calculations with the aid of appropriate tables.

The invention makes it possible to attain high measuring accuracy consistent with the Goldmann's technique and to eliminate inert gas (freon) from the measurement process, with an adequately simple construction arrangement of the tonometer sensor and with use in the data processing unit 17 of circuit design principles most commonly known in electronic-engineering practice. Provision of the applanation tonometer, according to the invention, with the sleeve 24 whose end is adapted to interact with the patient's eyeball and is concave-shaped in the form of the fragment of a sphere, ensures centering of the sensor on the patient's eye in the course of tonometry.

What we claim is:

1. An applanation tonometer, comprising:
   a housing;
   a rod positioned inside said housing and having a first end and a second end, and
   said first end being located outside said housing;
   plane-parallel springs holding said rod in position inside said housing;
   a contact disk made fast on said first rod end,
   a flat working surface of said disk interacting with the cornea and exerting force thereon;
   a unit for measuring said force applied to the corneal surface and converting said force into a signal suitable for processing, said unit being connected to said second end of said rod and having an output;
   a means for registering the instant of time when the diameter of an applanation circle on said corneal surface, formed due to the effect of said force exerted by said contact disk on said cornea, reaches a preset value, said registering means having an output; and
   a recording unit having a first input and a second input, said first input being connected to said output of the unit for measuring, and said second input being connected to said output of the means for registering; wherein
   said registering means comprises:
   a first sleeve having an inside diameter equal to said preset value of the applanation circle diameter and arranged coaxially with said rod carrying the contact disk and traversably along the axis of said rod,
   a flat end of said first sleeve most removed from said housing interacting with said cornea; and
   a contact set electrically connected to said second input of the recording unit and one of the contacts of said contact set being connected with said first sleeve,
   contacts of said contact set being closed by movement of said first sleeve at the instant when said working surface of the contact disk and said flat end of said first sleeve become coplanar in the course of mutual movement as a result of application of said force to said cornea.

2. An applanation tonometer as claimed in claim 1, further comprising:
   a second sleeve arranged coaxially with said first sleeve and axially traversable with respect to the first sleeve,
   the end of said second sleeve most removed from said housing being made concave in the shape of the fragment of a sphere.

* * * * *